(12) United States Patent
Boucher et al.

(10) Patent No.: US 6,344,648 B1
(45) Date of Patent: Feb. 5, 2002

(54) SYSTEM FOR DETECTION AND MEASUREMENT OF ONE OR SEVERAL GASES IN A GAS MIX

(75) Inventors: Daniel Boucher, Dunkerque; Philippe Charruyer; Alain Legrand, both of Bourges; Karine Michelet, Voisins le Bretonneux, all of (FR)

(73) Assignee: Aerospatiale Matra, Paris (FR)

(*) Notice: Subject to any disclaimer, the term of this patent is extended or adjusted under 35 U.S.C. 154(b) by 0 days.

(21) Appl. No.: 09/419,302

(22) Filed: Oct. 15, 1999

(30) Foreign Application Priority Data

Oct. 23, 1998 (FR) .............................. 98 13305

(51) Int. Cl.$^7$ ................................. G01J 5/02
(52) U.S. Cl. .................... 250/343; 250/339.13
(58) Field of Search ............................. 250/343, 339.13

(56) References Cited

U.S. PATENT DOCUMENTS

| | | | |
|---|---|---|---|
| 3,891,848 A | | 6/1975 | Fletcher et al. |
| 4,879,722 A | * | 11/1989 | Dixon et al. ................... 372/21 |
| 5,065,046 A | | 11/1991 | Guyer ......................... 359/330 |
| 5,317,156 A | | 5/1994 | Cooper et al. ............... 250/345 |
| 5,331,409 A | | 7/1994 | Thurtell et al. .............. 356/437 |
| 6,064,488 A | * | 5/2000 | Brand et al. ................. 356/440 |
| 6,134,004 A | * | 10/2000 | Reagen et al. .............. 356/451 |

FOREIGN PATENT DOCUMENTS

| | | |
|---|---|---|
| FR | 2 171 519 | 9/1973 |
| FR | 2 256 407 | 7/1975 |
| FR | 2 388 261 | 11/1978 |
| FR | 2 389 888 | 12/1978 |
| FR | 2 689 696 | 10/1993 |
| FR | 2 747 192 | 10/1997 |

OTHER PUBLICATIONS

Chen, W., et al., "Midinfrared cw Difference–Frequency Generation Using a Synchronous Scanning Technique for Continuous Tuning of the Full Spectral Region From 4.7 to 6.5 βm," *Rev. Sci. Instrum.*, 67 (10) Oct. 1996, pp. 3411–3415.

Vodopyanov KL, "Parametric generation of tunable infrared radiation in ZnGeP2 and GaSe pumped at 3 um", Sep. 1993, J. Opt. Soc. Am. B 10:1723–1729.*

* cited by examiner

*Primary Examiner*—Seungsook Ham
*Assistant Examiner*—Shun Lee
(74) *Attorney, Agent, or Firm*—Burns Doane Swecker & Mathis LLP

(57) ABSTRACT

A portable system for the real time detection and measurement of one or several gases is a gaseous mixture is disclosed. Such systems can be applied to industrial domains in which gases are to be measured and particularly toxic, dangerous, or polluting gases are generated. The system uses absorption spectrometry of a gas from a gaseous medium of interest. The optical means is at least two laser diodes with matchable cavities to generate a first and second wavelength, a light beam mixer prism, a double refraction crystal rotating on a controlled table. The tuned beam causes the gas to be measured to fluoresce and emit a signal to an infrared radiation detector which can indicate the identity and magnitude of the gas being measured.

10 Claims, 1 Drawing Sheet

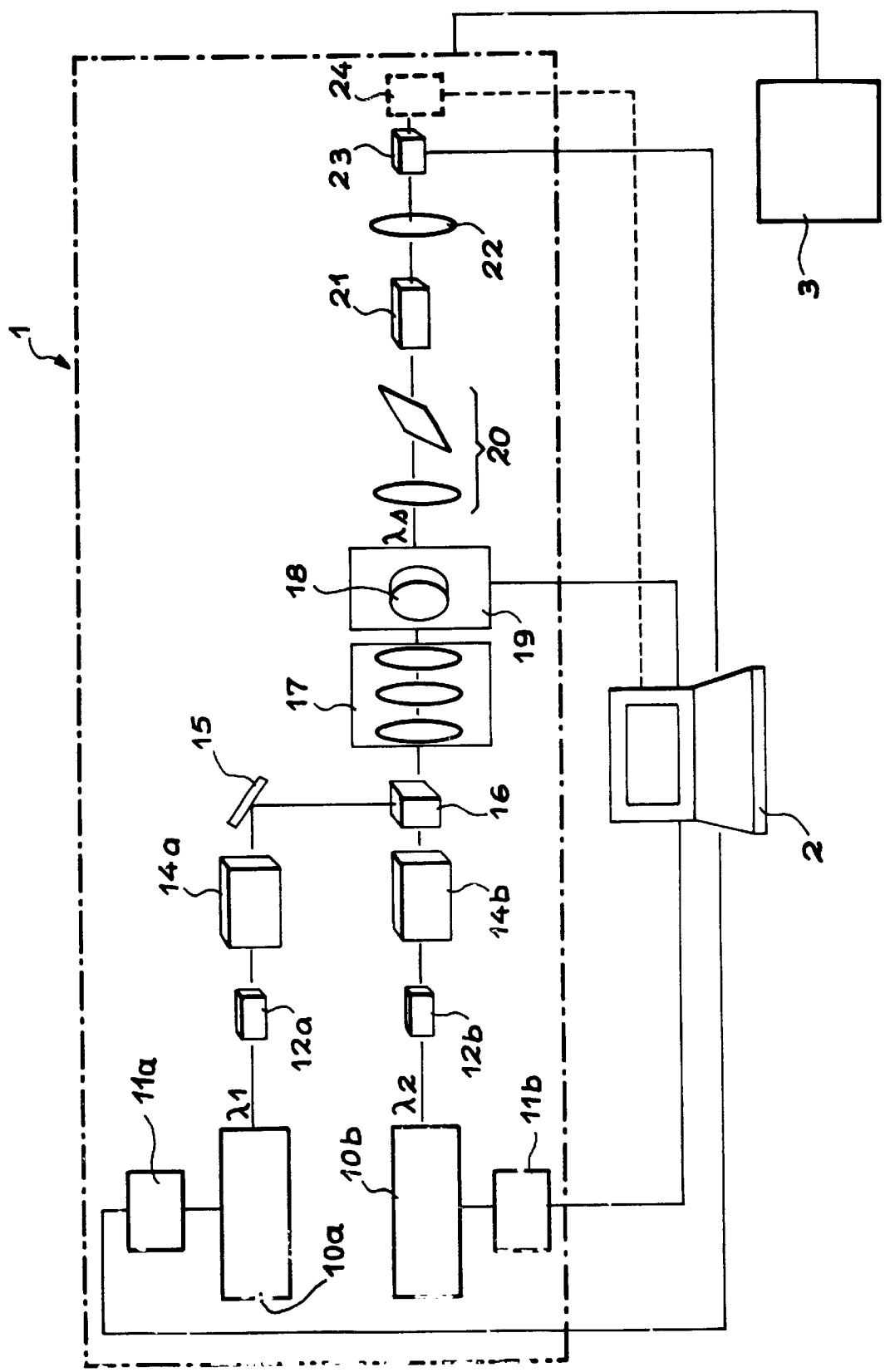

SYSTEM FOR DETECTION AND MEASUREMENT OF ONE OR SEVERAL GASES IN A GAS MIX

DOMAIN OF THE INVENTION

The invention relates to a portable system for the real time detection and measurement of one or several gases in a gas mix, and particularly atmospheric gases, by absorption spectrometry.

The invention is used in many industrial fields and particularly for industries generating gaseous waste released into the atmosphere such as refineries and thermal power stations, to determine the concentration of one or more toxic or dangerous gases, and in raw materials transformation industries such as the chemical and pharmaceutical industries, to check the atmosphere in which their employees are working. It is also used in atmospheric monitoring applications to determine the content of polluting gases in the atmosphere.

STATE OF THE ART

The principle of measuring gases in the atmosphere using the absorption spectrometry technique is well known to those skilled in the art. This technique consists of determining the absorption of an area of the atmosphere. This is done by illuminating the area of the atmosphere to be analyzed by a light source; therefore light passes through this area of the atmosphere. The light signal obtained after passing through this area of the atmosphere is retrieved and quantified on a detector in order to obtain information about the quantity of light transmitted, and consequently the quantity of light absorbed by the area of the atmosphere. The absorption spectrum of the measured gas is then determined. The gas to be measured is usually a known gas, and known gases are characterized spectroscopically by their absorption spectrum. Thus, gases present in the analyzed area of the atmosphere are recognized by comparing their absorption spectrum with the absorption spectrum determined by measurement with known spectra.

Many documents describe processes and devices for detecting gases in the atmosphere. Most of these devices use a laser source emitting a precise wave length. These documents include French patent applications FR-A-2 389 888, FR-A-2 388 261, FR-A-2171 519 and FR-A-2 256 407, and also French patent application FR-A-2 747 192. However, these devices have the disadvantage that they can only be used to measure a single gas selected in advance, since the choice of the laser source and the wave length that will be emitted by this laser source are directly related to the gas to be detected.

Furthermore, there is a device capable of emitting wave lengths that cannot be emitted by conventional laser sources. This device operates on the principle of frequency difference and is described in the following publications: "Midinfrared CW difference-frequency generation using a synchronous scanning technique for continuous tuning of the full spectral region from 4.7 to 6.5 $\mu$m", by W. CHEN, J. BURIE and D. BOUCHER, Rev. Sci. Instrum. Vol 67, No. 10, October 1996; "A novel CW optical Laser-based Difference-frequency infrared Spectrometer", by D. BOUCHER, W. CHEN, J. BURIE and P. PEZE, 5th conference on lasers and quantitative optics, Sep. 8–10, 1997, Strasbourg. This device comprises two titanium-sapphire (TiSa) lasers that generate infrared light radiation obtained by the difference between two light radiation beams initially emitted by the two lasers; the difference between the two initial radiation beams is obtained using a double refraction crystal. Different wavelengths can be obtained by varying this difference, so that several gases can be detected. However, this device requires the use of two lasers; therefore it is large and occupies an area of several square meters, and its weight exceeds one tonne. Therefore this device is difficult to move and cannot be used locally in the ambient atmosphere to be analyzed.

DESCRIPTION OF THE INVENTION

The purpose of the invention is to overcome these disadvantages. Consequently, it proposes an optical detection and quantitative measurement system for one or several gases in a gas mix, such as gases contained in the atmosphere. This system is compact and may be moved easily so that local gas analyses can be carried out in confined or semi-open spaces, even within the gas mix to be analyzed.

More precisely, the invention relates to a system for detection and measurement of a gas or several gases making up a gas mix, comprising:
- optical means for determining the absorption spectrum of the gas to be measured;
- means of storing data for different gases and for processing information output from optical means; and
- electrical power supply means for the optical means, characterized in that the optical means are placed within the gaseous medium to be analyzed and that they comprise:
- at least one first and one second laser diode with matchable cavities, emitting light beams with a first and a second wavelength, respectively;
- a light beam mixer prism;
- a double refraction crystal mounted on a rotating table forming an infrared light beam with a wavelength equal to the resultant of the difference between the first and second wavelengths (respecting phase matching conditions); and
- an infrared radiation detector.

Advantageously, the optical means comprise a multi-pass cell in which the light beam passes several times through the gaseous medium to be analyzed, to increase the measurement sensitivity.

The optical means may comprise a filter, allowing only infrared radiation to pass.

According to one embodiment of the invention, the system comprises means of checking the temperature and temperature compensation, in order to keep the laser diodes at a constant temperature.

According to one variant of the invention, the optical means and the storage and processing means are connected by radio or optical fibers.

The electrical power supply means for the device may consist of a battery so that the system is self-sufficient.

According to one particular embodiment of the invention, the double refraction crystal may for example be a gallium selenide crystal.

The system according to the invention may be associated with one or several other identical systems in a network.

BRIEF DESCRIPTION OF THE FIGURES

The single figure diagrammatically shows the various elements making up the spectroscopic frequency difference system according to the invention, with its optical means, storage and processing means, and its power supply means.

DETAILED DESCRIPTION OF EMBODIMENTS OF THE INVENTION

The invention relates to a system for the detection and the spectroscopic analysis of one or several gases in a gas mix such as the atmosphere. In general, this system can determine and measure any molecules in gaseous form that have an absorption spectrum in the infrared field.

Therefore, the purpose of this system is to quantitatively and qualitatively analyze several gases in the atmosphere within its own compact volume, in real time.

The system does this by continuously generating infrared light radiation within a wide spectral range, by frequency difference using two laser diodes with matchable cavities and a double refraction crystal. This system can thus generate wavelengths that cannot be achieved with conventional devices, such that several gases can be detected successively or simultaneously.

More precisely, the system according to the invention comprises optical means that determine the absorption spectrum of the gas(es) to be analyzed, means of storing data for the various known gases and for processing information obtained from the optical means more simply called processing means, and electrical power supply means for the entire system.

The optical means comprise at least two laser diode with matchable cavities, each of which emits a laser beam with a first wavelength λ1 called the "signal", and a second wavelength λ2 called the "pump", respectively.

The process and output frequency and power control means for this type of matchable cavity laser diodes are described particularly in French patent FR-A-2 689 696.

These two wavelengths λ1 and λ2 are then "mixed" by means of a double refraction crystal in order to obtain a wavelength λs different from λ1 and λ2. The use of a double refraction crystal to determine the frequency difference is explained by the fact that the refraction indexes in a double refraction crystal depend on the propagation and polarization directions of the incident waves, hence the non-linear nature of the frequency difference.

A combination of two diodes with matchable cavities and a double refraction crystal can scan a predefined spectral interval within the 2–20 μm range, for example between 8 and 12 μm. The value of this spectral interval depends on the values of the wavelengths λ1 and λ2, and the type of crystal used and its orientation. The wavelength λs may thus be equal to any value of the spectral interval defined by the laser diodes and the crystal, and particularly values that cannot be obtained by any device on the market. The spectral window thus created enables automatic and continuous adjustment of the wavelength λs as a function of the gases to be analyzed.

According to one example of the system according to the invention, a laser diode with an external cavity reference DL 200/857 nm and laser diode DL 20/941 nm can be chosen as laser diodes, both manufactured by the OPTON LASER INTERNATIONAL® Company. These two diodes make use of the same technology but have a different central match. When this pair of laser diodes is associated with a gallium selenide (GaSe) crystal, an 8 to 12 μm spectral window is created.

According to another example of the system according to the invention, an $AgGaSe_2$ crystal can be associated with the same pair of laser diodes which gives a slightly higher spectral window.

In the example described above, the laser diodes and the double refraction crystal are chosen to enable detection of gases with their absorption spike within the 8–12 μm interval, since the absorption spike of many polluting gases is within this interval.

These gases include formic acid HCOOH, carbon dioxide $CO_2$, methane $CH_4$, sulfuric acid $H_2S$, ammonia $NH_3$, nitrogen dioxide $NO_2$, nitrogen protoxide $N_2O$, ozone $O_3$, water $H_2O$, ethane $C_2H_6$, acetylene $C_2H_2$, ethylene $C_2H_4$, propane $C_3H_8$, methyl chloride $CH_3Cl$, propylene $C_3H_6$, methanol $CH_4O$, benzene $C_6H_6$, toluene $C_7H_8$, freon 114 $C_2Cl_2F_4$, tetrachloromethane $CCl_4$, freon 11 $CCl_3F$, freon 12 $CCl_2F_2$, sulfur fluoride $SF_6$, etc.

However, it is quite possible to determine and to quantify gases for which the absorption spike is outside this 8–12 μm range; this is done simply by choosing laser diodes that can be matched at different frequencies and choosing a more appropriate double refraction crystal; the phase match can be obtained for another spectral window by adjusting the adjustment parameters for the entire system.

The above description relates to an embodiment in which the system comprises two laser diodes. However, in order to obtain wider wavelength scanning, in other words a wider spectral window, the system may comprise a laser diode with fixed frequency and several matchable laser diodes. This variant has the additional advantage that the possible frequency range can be quickly modified.

As described above, the role of the double refraction crystal is to enable a mix of two wavelengths (or frequencies) emitted by the laser diodes. This is done by installing the double refraction crystal on a plate, or rotating table, controlled by the processing means which will be described in more detail later. The crystal can be rotated at a rotation angle of about ±10° in order to modify the mix proportion between the two wavelengths λ1, and λ2. The phase match is obtained by adjusting the two diodes and rotating the crystal support plate.

In practice, the rotation of the laser diodes may be adjusted in one, two or three directions depending on the selected embodiment. Furthermore, the rotating table 19 may be rotated about one, two or three axes. Furthermore, the diode settings can be adjusted based on three or four data depending on the embodiment.

The figure diagrammatically shows the preferred embodiment of the system according to the invention with its optical and electro-optical means reference 1, its storage and processing means reference 2, and its electrical power supply means reference 3.

The optical means 1 comprise the two laser diodes with external cavities 10a and 10b each of which emits a light beam with wavelength λ1 and λ2 respectively. The diode 10b is mounted such that the beam output from it is polarized at 90° with respect to the beam output from diode 10a.

According to the embodiment shown in the figure, the two light beams are each inserted in a Faraday isolator, references 12a and 12b respectively. These Faraday isolators 12a and 12b are devices which are designed to prevent any back scattering on the diodes.

Each of the light beams output from the Faraday isolators 12a and 12b is then input into an anamorphic prism, 14a and 14b respectively. These anamorphic prisms 14a and 14b are designed to make the light beams output from the diodes cylindrical, and to facilitate focusing them in the double refraction crystal.

The light beams obtained at the output from these anamorphic prisms 14a and 14b then pass through a polarizing cube reference 16. The role of this polarizing cube 16 is to assemble the two beams so that they then follow the same optical path, respecting their polarization. For example, one of the beams can directly pass through the polarizing cube;

the other beam, directed towards the cube through a mirror type reflector 15, may be reflected at an angle of 90° by the polarizing cube 16. In other words, the polarizing cube 16 is a switch that directs each of the two beams to the double refraction crystal 18, colinearly.

A telescope 17 may be inserted between the double refraction crystal 18 and the polarizing cube 16, in order to focus the light beam output from the polarizing cube onto the crystal 18.

As explained earlier, the double refraction crystal 18 installed on a rotating table 19 then mixes the $\lambda 1$ and $\lambda 2$ wavelengths in order to obtain a beam with a wavelength $\lambda s$ at its output. This "mix" may be modified by changing the control parameters for the two diodes 10a and 10b and rotating the crystal 18 by means of rotating table 19.

According to one embodiment of the invention, a filter Ge reference 20 is placed at the output from this double refraction crystal 18. The role of this filter 20 is to allow infrared radiation only to pass so as to facilitate detection of the absorption spectrum of the gas to be analyzed. A multipass cell 21 at the output from this filter 20 enables multiple passes of the light beam through the area containing the gaseous mix to be analyzed. For example, this multipass cell may be a white cell consisting of a sort of cylinder with its ends closed by two hemispheres that perform several successive reflections of the light beam in order to increase the length of the path of the light beam through the area containing the gaseous mix to be analyzed. This multipass cell 21 thus increases the sensitivity of the system.

A lens 22 at the output from this white cell 21 converges the light beam towards the infrared detector 23. This infrared detector 23 determines the absorption spectrum of the gas to be analyzed, starting from the received light beam. This infrared detector may be a quite conventional HgCdTe detector; therefore it will not be described in more detail.

Data for the detected absorption spectrum are sent to processing means 2 that then carry out the necessary processing to determine the nature (i.e., quantitatively) of the gas and to calculate the concentration (i.e., quantitatively) of this gas.

The parameters are diode power supply currents, temperatures, the position of the matching network (mirror moved in translation in order to modify the cavity length, which modifies the wave length) and the beam orientation. Control of these parameters can generate single mode radiation with wavelengths $\lambda 1$ and $\lambda 2$ in accordance with the value of the angle of rotation of crystal 18 in order to obtain the required infrared beam. Means 11a and 11b are implemented on electronic boards so that they can be integrated in storage and processing means 2.

According to the embodiment shown in solid lines in the figure, the system operates in open loop, in other words without any measurement and without servocontrol of the frequency collected by the infrared detector 23, which means that it is accepted that the frequencies of the beams output from the two diodes are the required frequencies for the cavity matching parameters.

According to another embodiment of the invention, means 24 for measuring the frequency collected by the infrared detector 23 may be inserted at the output from the infrared detector. These frequency measurement means 24 shown in dashed lines in the figure are connected to the processing means 2 that determine any difference, and that modify diode matching to correct this difference.

The storage and processing means 2 may simply be a PC type computer on which a database is installed with a measurements operating software which supplies measurements about the presence and content of the searched gas, in real time.

The database comprises all known information about all known gases, and particularly information about absorption spikes of each of the gaseous molecules that the system is capable of analyzing.

Advantageously, this database may be regularly updated whenever new gaseous molecules or gases are discovered or manufactured. For example, this database could be the base marketed by the HITRAN® Company.

In practice, the operator attempts to detect and quantify one or several specific gas(es) with known absorption spikes listed in the spectroscopic database contained in the computer. Wavelengths of these spikes correspond to the infrared wavelengths that the system will have to generate. Consequently, all the operator has to do is to enter the nature of the searched gas in the PC; the choice of frequencies F1 and F2 of the laser diodes 10a and 10b, and consequently wavelengths $\lambda 1$ and $\lambda 2$ emitted by these diodes, and the position of the crystal, are calculated automatically by the PC computer.

Therefore the PC computer controls the laser diode parameters and rotation of the crystal rotating table 19. It also enables acquisition and real time processing of the measurements, particularly to determine the concentration of gases detected.

Gas measurements may be made specifically when required, or continuously for one or several gases simultaneously or successively and possibly periodically.

According to one embodiment of the invention, the optical means may be connected to a transmitter-receiver that makes a radio link with a transmitter-receiver connected to the PC computer.

According to another embodiment, the link between optical means and the computer may make use of optical fibers.

According to one variant, several systems according to the invention identical to each other may be connected in a network, on a single site or on several sites. In this case, the distributed sites may be managed either from one of the systems, or by a central system.

In practice, a calibration will be necessary when the system is first started. This will consist of using a known gas as a reference and making measurements using this gas. The results obtained from measurements of this known gas are used to calibrate the system and possibly to input correction coefficients.

According to one variant, this calibration may be made using two (or more) samples of control gases with absorption spikes at each end of the frequency window, and permanently installed in the system.

As will have become obvious from the above description, all parts of optical assemblies in the system according to the invention are small, and therefore the entire system is compact; it occupies significantly less than one square meter, and may be installed in a case. Consequently, it is easily transportable, so that it can be used locally (which means that it is placed directly in the area containing the gaseous mix to be analyzed).

In order to facilitate its local use, the system may be provided with a battery electrical power supply reference 3 in the figure, which gives it an endurance of about 1 to 5 days.

However, the system may be powered with electricity from the mains power supply, for example for a system installed permanently at a site.

Since the system is used for "local" detections, the optical elements are likely to become dirty. The system should include manual or automatic means of cleaning the lenses.

Note also that the sensitivity of the system is of the order of 10 ppb (parts per billion), which means that a gas can be detected starting from a concentration in the atmosphere of 10 billionths. The resolution of this system is of the order of 100 MHz.

What is claimed is:

1. System for detection and measurement of at least a gas of a gaseous medium, comprising:

optical means (1) for determining the absorption spectrum of the gas to be measured;

means (2) of storing data for different gases and for processing information output from optical means; and electrical power supply means (3); characterized in that the optical means are placed within the gaseous medium to be analyzed and comprise:

at least one first and one second laser diode with matchable cavities (10a, 10b), emitting light beams at first and a second wavelengths ($\lambda 1$, $\lambda 2$) respectively;

a light beam mixer prism (16);

a double refraction crystal (18) mounted on a rotating table (19) forming an infrared light beam with a wavelength equal to the resultant of the difference between the first and second wavelengths, said rotating table being controlled by said means for processing information; and an infrared radiation detector (23) receiving said infrared light beam and detecting the absorption spectrum of the gas to be measured, said absorption spectrum detected by said detector being processed by said means for processing information with the stored data related to the different gases in order to analyze quantitatively and qualitatively said gas of the gaseous medium.

2. System according to claim 1, characterized in that the optical means comprises a multipass cell (21) in which the infrared light beam passes several times through the gaseous medium to be analyzed.

3. System according to claim 1, characterized in that the optical means optionally comprises a filter (20) allowing only infrared radiation to pass.

4. System according to claim 1, characterized in that said system comprises means (11a, 11b) of checking parameters in order to obtain single mode radiation.

5. System according to claim 1, characterized in that the optical means and the means of storing data for different gases and for processing information are connected to each other by radio or optical fiber.

6. System according to claim 1, characterized in that the electrical power supply means consist of a battery.

7. System according to claim 1, characterized in that the double refraction crystal is a gallium selenide crystal.

8. System according to claim 1, characterized in that said system comprises means of verifying diode matching frequencies, connected in a closed loop with said means for processing information and said laser diodes.

9. System according to claim 1, characterized in that said system is connected through a network to one or several identical systems.

10. System according to claim 6, characterized in that the double refraction crystal is a gallium selenide crystal.

* * * * *